United States Patent [19]

Kurozumi

[11] Patent Number: 5,206,416
[45] Date of Patent: Apr. 27, 1993

[54] ISOCARBACYCLIN DERIVATIVE

[75] Inventor: Seizi Kurozumi, Kokubunji, Japan

[73] Assignee: Teijin Limited, Osaka, Japan

[21] Appl. No.: 764,068

[22] Filed: Sep. 24, 1991

Related U.S. Application Data

[63] Continuation of Ser. No. 536,752, Jun. 12, 1990, abandoned, which is a continuation-in-part of Ser. No. 905,976, Sep. 11, 1986.

[30] Foreign Application Priority Data

Sep. 13, 1985 [JP] Japan .................. 60-201716
Oct. 14, 1985 [JP] Japan .................. 60-226973
Oct. 14, 1985 [JP] Japan .................. 60-226974

[51] Int. Cl.$^5$ .................................. C07C 177/00
[52] U.S. Cl. ......................... 560/119; 560/116; 562/498; 562/501
[58] Field of Search ........... 560/119, 116; 562/501, 562/498

[56] References Cited

U.S. PATENT DOCUMENTS 4,788,319 11/1988 Hazato ................... 560/11

FOREIGN PATENT DOCUMENTS 247740 12/1987 European Pat. Off. .
19505 1/1987 Japan .................. 560/119
132839 6/1987 Japan .................. 560/119
242643 10/1987 Japan .................. 560/119
63-303962 12/1988 Japan .

Primary Examiner—Robert Gerstl
Attorney, Agent, or Firm—Sherman and Shalloway

[57] ABSTRACT

An isocarbacyclin derivative represented by the following formula:

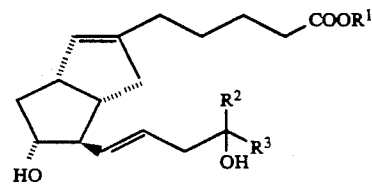

wherein $R^1$ represents H or a linear or branched $C_1$-$C_{10}$ alkyl group, $R^2$ represents H, a methyl group or a vinyl group, and $R^3$ represents an unsubstituted linear or branched $C_3$-$C_8$ alkyl group or a $C_5$-$C_6$ cycloalkyl group. and a pharmaceutaically acceptable salt thereof.

5 Claims, No Drawings

ISOCARBACYCLIN DERIVATIVE

This application is a continuation of application Ser. No. 536,752 now abandoned, which in turn is a divisional continuation-in-part of copending application Ser. No. 905,976 filed Sep. 11, 1986.

This invention relates to 3,6,7-trisubstituted-bicyclo[3.3.0]-2-octenes, i.e. 15-deoxy-16-hydroxy 9(O)-methano-$\Delta^{6(9\alpha)}$-prostagrandins $I_1$ (isocarbacyclin derivatives). More specifically, this invention relates to novel isocarbacyclin derivatives useful as medicines such as a cardiovascular agent, an antiulcer agent, a cell protecting agent and a tissue-injury healing agent.

Carbacyclins are prostaglandin $I_2$ analogs resulting from substitution of methylene groups for the oxygen atoms at the 6,9α-positions of prostaglandin (to be sometimes abbreviated as PG) $I_2$ (PGI$_2$), an in vivo physiologically active substance. Since carbacyclins are chemically more stable than natural prostaglandin $I_2$ having an enol ether partial structure in the molecule, they are useful as pharmaceuticals such as an antithrombotic agent. It was recently discovered that isocarbacyclins, a double bond isomer of carbacyclin, namely 9(O)-methano-$\Delta^{6(9\alpha)}$-prostaglandins $I_1$, show the strongest platelet aggregation inhibitory activity among these analogs, and are expected to have application as medicines [see Ikegami et al., Tetrahedron Letters, 33, 3493 and 3497 (1983) and Japanese Laid-open Patent Publication Nos. 137445/84 and 210044/84].

Several examples of the production of the 9(O)-methano-$\Delta^{6(9\alpha)}$-prostaglandin $I_1$ (isocarbacyclin) have previously been known. The outlines of the methods, key synthetic intermediates used in these examples and the literature references describing them are summarized as follows:

(1) Ikegami et al. Testrahedron Letters, 24, 3493 (1983) and Chemistry Letters, 1069 (1989):

(2) Ikegami et al. Tetrahedron Letters, 24, 3497 (1983)

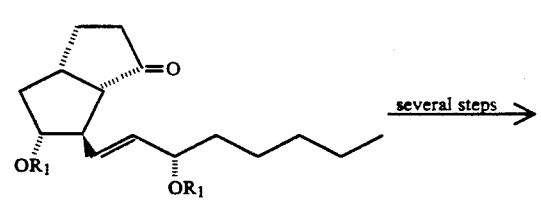

(3) Ikegami et al., J. Chem. Soc., Chemical Communications, 1602 (1984):

(4) Shibasaki et al., Tetrahedron Letters, 25, 5087 (1984):

-continued

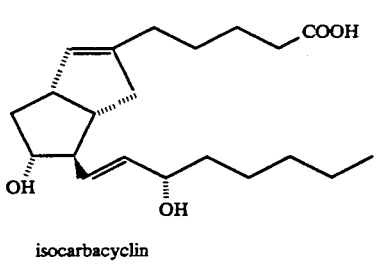

isocarbacyclin (5) Shibasaki et. al., Tetrahhedron Letters, 25, 1067 (1984):

PGE$_2$ —several steps→

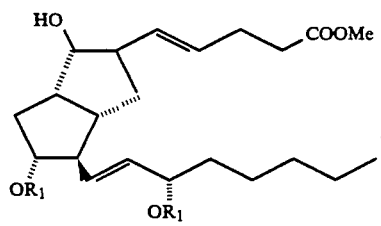

key intermediate

—several steps→

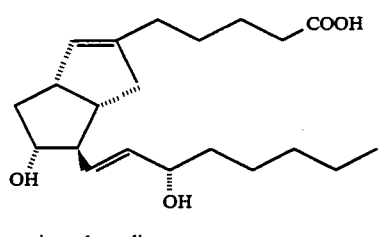

isocarbacyclin (6) Kojima et al., Chem. Pharm. Bull., 32, 2866 (1984):

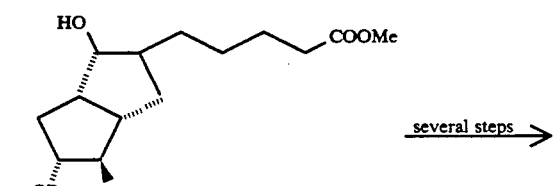

key intermediate

—several steps→

-continued

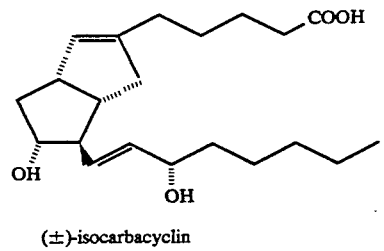

(±)-isocarbacyclin (7) Kojima et al., Japanese Laid-Open Patent Publication No. 28943/1985:

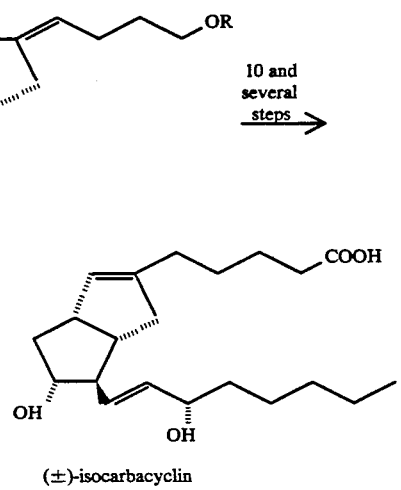

(±)-isocarbacyclin

Methods (1) and (5) uses PGE$_2$ as a starting material, and through several steps, it is converted to a key intermediate, and after further several steps, the final product, isocarbacyclin, is obtained. They can hardly be said as industrial methods.

Methods (2) and (3) require a multiplicity of steps starting from expensive Corey lactone in order to obtain the corresponding starting materials and key intermediates, and the total yield of the final product is not high. They cannot necessarily be said as industrially advantageous methods.

According to methods (6) and (7), the final product is obtained only in the form of a DL isomer. They cannot be said as methods to produce medicines.

Finally, method (4) is one in which the starting material can easily be obtained from optically active (R)-4-hydroxy-2-cyclopentenone by the method of the present inventors (Japanese Laid-open Patent Publication No. 155116/1982) and besides the key intermediate can be formed from the starting material industrially without any problem. However, said method has the great disadvantage that the total yield is decreased since in the steps from the key intermediate to the final isocarbacyclin, various difficulties arise such as the use of an organic mercury compound, the loss of the regiospecificity of the compounds, and the inclusion of inseparable by-products. It cannot be thus a practical, industrial method.

Meanwhile, in order to produce medicines from artificial PGI$_2$ analogs including such isocarbacyclin derivatives, it is inevitable to suppress a ratio of a physiological activity as a side effect to a main physiological activity and selectively exhibit the desirous physiological activity alone.

It is an object of this invention to provide 3,6,7-trisubstituted-bicyclo[3.3.0]-2-octenes, i.e. 15-deoxy-16-hydroxy-9(O)-methano- $\Delta^{6(9\alpha)}$-prostaglandins $I_1$ (isocarbacyclin derivatives).

Another object of this invention is to provide isocarbacyclins having an improved specific physiological activity among various physiological activities provided by $PGI_2$ analogs, i.e. an improved selectivity of activity.

Still another object of this invention is to provide isocarbacyclins useful as a cardiovascular agent, an antiulcer agent, a cell protecting agent and a tissue-injury healing agent.

The other objects and advantages of this invention will be made clear from the following explanation.

According to this invention, such objects and advantages of this invention can be achieved by an isocarbacyclin derivative represented by the following formula (I)

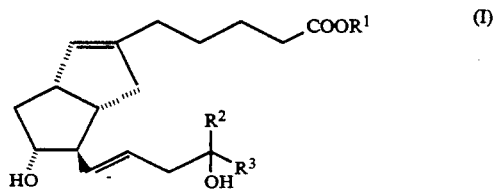

wherein $R^1$ represents H or a linear or branched $C_1$-$C_{10}$ alkyl group, $R^2$ represents H, a methyl group or a vinyl group, and $R^3$ represents an unsubstituted linear or branched $C_3$-$C_8$ alkyl group, or a $C_5$-$C_6$ cycloalkyl group, and a pharmaceutically acceptable salt thereof.

In formula (I), $R^1$ represents a hydrogen atom or a linear or branched $C_1$-$C_{10}$ alkyl group. Examples of the linear or branched $C_1$-$C_{10}$ alkyl group include methyl, ethyl, n-propyl, isopropyl, n-butyl, isobutyl, sec-butyl, tert-butyl, pentyl, hexyl, 3-methylbutyl, 4-methylpentyl, octyl and decyl groups. Of these, the methyl, ethyl, isopropyl, isobutyl and tert-butyl groups are preferable. The methyl and tert-butyl groups are most preferable.

In formula (I), $R^2$ represents a hydrogen atom, a methyl group or a vinyl group.

In formula (I), $R^3$ represents an unsubstituted linear or branched $C_3$-$C_8$ alkyl group or a $C_5$-$C_6$ cycloalkyl group.

Examples of the linear or branched $C_3$-$C_8$ alkyl groups include propyl, butyl, pentyl, hexyl, heptyl, 2-hexyl, 2-methyl-2-hexyl, 2-methylbutyl, 2-methylpentyl, 2-methylhexyl and 2,2-dimethylhexyl groups. Of these, the butyl, pentyl, hexyl, heptyl, 2-hexyl, 2-methyl-2-pentyl, 2-methylbutyl and 2-methylhexyl groups are preferable.

Examples of the $C_5$-$C_6$-cycloalkyl group include cyclopentyl and cyclohexyl groups.

In the isocarbacyclin derivatives represented by formula (I), the carbon atom by which $R^2$ and $R^3$ are bound is an asymmetrical carbon atom. The isocarbacyclin derivatives of this invention include either of steric isomers relative to the asymmetrical carbon atom and a mixture of these steric isomers at an arbitrary ratio.

Preferable examples of the 3,6,7-trisubstituted-bicyclo[3.3.0]-2-octenes represented by formula (I) which are provided by this invention are as follows.

Most preferable among the aforesaid compounds are the compounds (08), (09) and (10) (15-deoxy-16-hydroxy-16-methyl-9(O)-methano-$\Delta^{6(9\alpha)}$-prostaglandins $I_1$) of formula

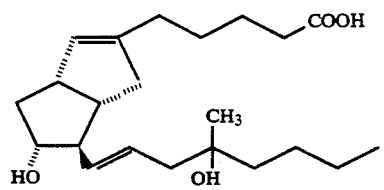

and the compound (16) (15-deoxy-16-hydroxy-16-vinyl-9(O)-methano-$\Delta^{6(9\alpha)}$-prostaglandin $I_1$) of formula.

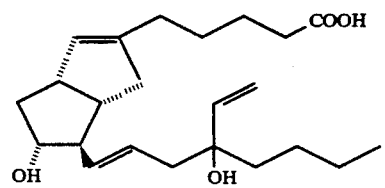

The 3,6,7-trisubsituted-bicyclo[3,3,0]-2-octenes represented by formula [I] are produced by reacting 6,7-disbustituted -2-hydroxy-3-methylenebicyclo[3,3,0] octanes represented by formula (II)

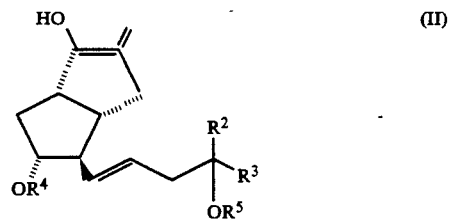

wherein $R^4$ and $R^5$ are identical or different and each represents a tri($C_1$-$C_7$) hycrocarbonsilyl group or a group forming an acetal linkage together with the oxygen atom of the hydroxyl group, and $R^2$ and $R^3$ are the same as defined above, with an organolithium in an organic solvent and then with cuprous iodide and further with an organolithium compound represented by the following formula (III)

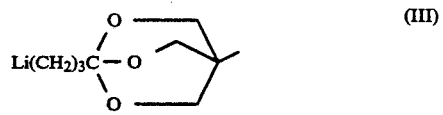

in the presence of N,N-methylphenylaminotributylphosphonium iodide, and then subjecting the resulting product to a deprotection reaction, a hydrolysis reaction and an esterification reaction.

The 6,7-disubstituted-2-hydroxy-3-methylenebicyclo[3.3.0]octane used as a starting material in this invention is a known compound and is formed by a process proposed separately by the present inventors. Namely, the 6,7-disubstituted-3-hydroxymethylbicyclo[3.3.0]-2-octene formed by the process described in the aforesaid literature [M. Shibasaki et al., Tetrahedron Letters, 25, 5087 (1984)], etc. is used as a starting material and converted into a compound represented by formula (II) as the starting material in the process of this invention through the following synthesis route.

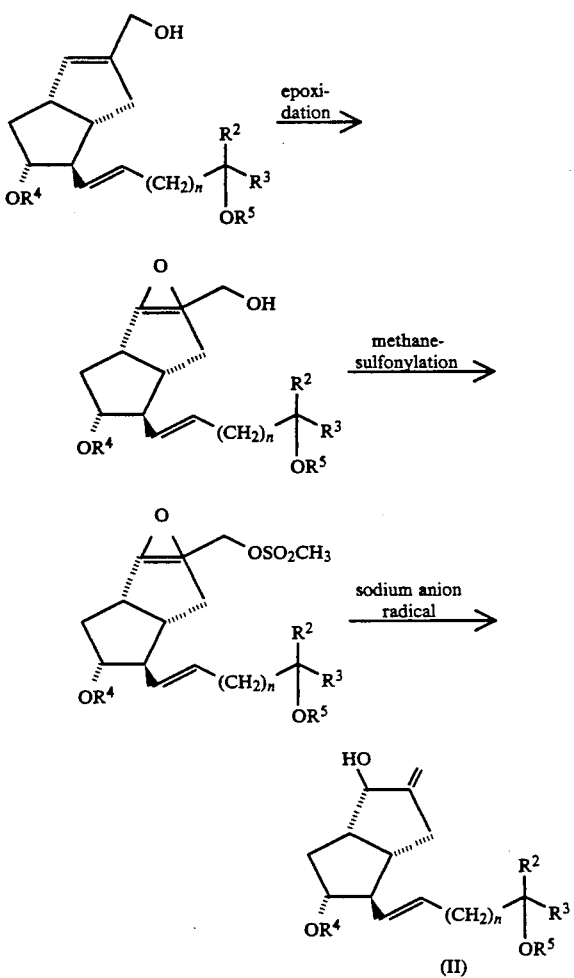

In formula (II), $R^4$ and $R^5$ are identical or different and each represents a hydrogen atom, a tri($C_1$–$C_7$)hydrocarbonsilyl group or a group forming an acetal linkage together with the oxygen atom of the hydroxyl group.

Refereable examples of the tri($C_1$–$C_7$)-hydrocarbonsilyl group are tri($C_1$–$C_4$) alkylsilyl groups such as trimethylsilyl, triethylsilyl, triisopropylsilyl and tert-butyldimethylsilyl groups; diphenyl($C_1$–$C_4$)-alkylsilyl groups such as a tert-butyldiphenylsiyl group; di($C_1$–$C_4$) alkylphenylsilyl groups such as a dimethyl-phenylsilyl group; and a tribenzylsilyl group. Of these, the tri($C_1$–$C_4$)alkylsilyl groups, the diphenyl ($C_1$–$C_4$)alkylsilyl groups and the di($C_1$–$C_4$)alkylphenylsilyl groups are preferable. The tert-butyldimethylsilyl group and the trimethylsilyl group are most preferable. Examples of the group forming the acetal linkage together with the oxygen atom of the hydroxyl group are methoxymethyl, 1-ethoxyethyl, 2-methoxy-2-propyl, 2-ethoxy-2-propyl, (2-methoxyethoxy)methyl, benzyloxymethyl, 2-tetrahydropyranyl and 2-tetrahydrofuranyl groups.

$R^2$ and $R^3$ are the same as defined above, and preferable examples are those taken in formula (I). Examples of the 6,7-disubstituted-2-hydroxy-3-methylenebicyclo[3.3.0]octane represented by formula (II) are starting compounds corresponding to the examples of the 3,6,7-trisubstituted bicyclo[3.3.0]-2-octenes represented by formula (I).

(01) (1S,5S,6S,7R)-3-(4-carboxybutyl)-6-[(E)4-hydroxy-1-octenyl]-7-hydroxybicyclo[3.3.0]-2-octene,
(02) (1S,5S,6S,7R)-3-(4-carboxybutyl)-6-[(E)4-hydroxy-1-nonenyl]-7-hydroxybicyclo[3.3.0]-2-otene,
(03) (1S, 5S,6S,7R)-3-(4-carboxybutyl)-6-[(E)4-hydroxy-1-decenyl]-7-hydroxybicyclo[3.3.0]-2-otene,
(04) (1S,5S,6S,7R)-3-(4-carboxybutyl)-6-[(E)4-hydroxy-5-methyl-1-nonenyl]-7-hydroxybicyclo[3.3.0]-2-otene,
(05) (S1,5S,6S,7R)-3-(4-carboxybutyl)-6-[(E)4-hydroxy-5,5-dimethyl-1-octenyl]-7-hydroxybicyclo[3.3.0]-2-otene,
(06) (1S,5S,6S,7R)-3-(4-carboxybutyl)-6-[(E)4-hydroxy-4-cyclopentyl-1-butenyl]-7-hydroxybicyclo[3.3.0]-2-otene,
(07) (1S,5S,6S,7R)-3-(4-carboxybutyl)-6-[(E)4-hydroxy-4-cyclohexyl-1-butenyl]-7-hydroxybicyclo[3.3.0]-2-otene,
(08) (1S,5S,6S,7R)-3-(4-carboxybutyl)-6-[(E)4-hydroxy-4-methyl-1-octenyl]-7-hydroxybicyclo[3.3.0]-2-otene,
(09) (1S,5S,6S,7R)-3-(4-carboxybutyl)-6-[(E,4S)-4-hydroxy-4-methyl-1-octenyl]-7-hydroxybicyclo[3.3.0]-2-otene,
(10) (1S,5S,6S,7R)-3-(4-carboxybutyl)-6-[(E,4R)-4-hydroxy-4-methyl-1-octenyl]-7-hydroxybicyclo[3.3.0]-2-otene,
(11) (1S,5S,6S,7S)-3-(4-carboxybutyl)-6-[(E)4-hydroxy-4-methyl-1-nonenyl]-7-hydroxybicyclo[3.3.0]-2-otene,
(12) (1S,5S,6S,7R)-3-(4-carboxybutyl)-6-[(E)4-hydroxy-4,5-dimethyl-1-nonenyl]-7-hydroxybicyclo[3.3.0]-2-octene,
(13) (1S,5S,6S,7R)-3-(4-carboxybutyl)-6-[(E)4-hydroxy-5-methyl-1-octenyl]-7-hydroxybicyclo[3.3.0]-2-octene,
(14) (1S,5S,6S,7R)-3-(4-carboxybutyl)-6-[(E)4-hydroxy-4-methyl-4-cyclopentyl-1-butenyl]-7-hydroxybicyclo[3.3.0]-2-octene,
(15) (1S,5S,6S,7R)-3-(4-carboxybutyl)-6-[(E)4-hydroxy-4-methyl-4-cyclohexyl-1-butenyl]-7-hydroxybicyclo[3.3.0]-2-octene,
(16) (1S,5S,6S,7R)-3-(4-carboxybutyl)-6-[(E)4-hydroxy-4-vinyl-1-octenyl]-7-hydroxybicyclo[3.3.0]-2-octene,
(17) (1S,5S,6S,7R)-3-(4-carboxybutyl)-6-[E)4-hydroxy-4-vinyl-1-nonenyl]-7-hydroxybicyclo[3.3.0]-2-octene,
(18) (1S,5S,6S,7R)-3-(4-carboxybutyl)-6-[(E)4-hydroxy-4-vinyl-5-methyl-1-nonenyl]-7-hydroxybicyclo[3.3.0]-2-octene,
(19) (1S,5S,6S,7R)-3-(4-carboxybutyl)-6-[(E)4-hydroxy-4-vinyl-4-cyclopentyl-1-butenyl]-7-hydroxybicyclo[3.3.0]-2-octene,
(20) (1S,5S,6S,7R)-3-(4-carboxybutyl)-6-[(E)4-hydroxy-4-vinyl-4-cyclohexyl-1-butenyl]-7-hydroxybicyclo[3.3.0]-2-octene,
(21) (1S,5S,6S,7R)-3-(4-carboxybutyl)-6-[(E)4-hydroxy-7-methyl-1,6-octadienyl]-7-hydroxybicyclo[3.3.0]-2-octene,
(22) (1S,5S,6S,7R)-3-(4-carboxybutyl)-6-[(E)4-hydroxy-6-methyl-1,7-nonadienyl]-7-hydroxybicyclo[3.3.0]-2-octene,
(23) (1S,5S,6S,7R)-3-(4-carboxybutyl)-6-[(E)4-hydroxy-9-methyl-1,8-decanedienyl]-7-hydroxybicyclo[3.3.0]-2-octene,
(24) methyl esters of compounds (01) to (23),
(25) ethyl esters of compounds (01) to (23),

(26) isopropyl esters of compounds (01) to (23),
(27) tert-butyl esters of compounds (01) to (23),
(28) hexyl esters of compounds (01) to (23), and
(29) decyl esters of compounds (01) to (23).

In the process of this invention, the 6,7-disubstituted-2-hydroxy-3-methylenebicyclo[3.3.0]octane of formula (II) is reacted with an organolithium in an organic medium and then with cuprous iodide and further with an organolithium compound of formula (III) in the presence of N,N-methylphenylaminotributylphosphonium iodide, and the resulting product is further subjected to the deprotection reaction, the hydrolysis reaction and the esterification reaction to form the final 3,6,7-trisubstituted-bicyclo[3.3.0]-2-octene of formula (I).

The above reaction is performed basically in accordance with the method of Y. Tanigawa et al. described in J. Am. Chem. Soc., 100, 4610 (1978).

Preferable examples of the organolithium used in the above process are n-butyllithium and methyllithium. The amount of the organolithium is 0.8 to 1.5 moles, preferably 1.0 to 1.2 moles, per mole of the 6,7-disubstituted-2-hydroxy-3-methylenebicyclo[3.3.0]octane. The reaction temperature is −78° C. to 50° C., preferably −40° C. to 25° C. The reaction time, which varies depending on the reaction temperature, is, for example, about 30 minutes at 20° C. In the process of this invention, the 6,7-disubstituted-2-hydroxy-3-methylenebicyclo-8 3.3.0]octane of formula (II) is formed into its lithium alkoxide by this reaction step.

Subsequently, the solution is reacted with cuprous iodide to form a solution of an organic copper lithium compound. The amount of the cuprous iodide is 0.8 to 1.5 moles, preferably 1.0 to 1.2 moles, per mole of the compound of formula (II). The reaction temperature is −100° C. to 50° C., preferably −78° C. to 25° C. The reaction time, which varies depending on the reaction temperature, about 30 minutes at 20° C.

In the process of this invention, the reaction is carried out by further adding an organolithium compound represented by the following formula (III)

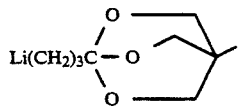

to the above solution of the organic copper lithium compound.

The organolithium compound can easily be obtained from the corresponding bromide and iodide by the reaction with t-butyllithium or a lithium anion radical solution (such as naphthalene, 1-(N,N-dimethylamino)naphthalene, 4,4'-di-tert-butylbiphenyl or ammonia).

The amount of the organolithium compound is 0.8 to 20.0 moles, preferably 1.0 to 10.0 times, especially preferably 1.2 to 5.0 moles, per mole of the compound of formula (II). The reaction temperature is −100° C. to 0° C., preferably −78° C. to −40° C. The reaction time is about 10 to 30 minutes.

The reaction is finally performed by adding N,N-methylphenylaminotributylphosphonium iodide. A method of synthesizing this reactant is reported in the literature of Y. Tanigawa, et al. Especially, this reactant is preferably added in the form of a solution in N,N-dimethylformamide.

The amount of the reactant is 0.8 to 5.0 moles, preferably 1.0 to 3.0 moles, most preferably 1.1 to 3.0 moles, per mole of the compound of formula (II). The reaction temperature is −100° C. to 50° C., preferably −78° C. to 25° C. The reaction time is several hours at 25° C.

Such reaction is run in an organic medium from the initial stage. Examples of the organic medium are hexane, benzene, ether, tetrahydrofuran, dimethoxyethane, dioxane, methylene chloride and N,N-dimethylformamide. They may be used either singly or in combination. Hexane, tetrahydrofuran and N,N-dimethylformamide are most preferable. The amount of the organic medium may be an amount in which the reaction smoothly advances. Usually, it is 1.0 to 100.0 volumes, preferably 5.0 to 50.0 volumes, per volume of the reaction product.

The thus obtained reaction solution may be treated in a usual manner. For example, a sparingly water-soluble organic solvent such as hexane, pentane, petroleum ether, ethyl ether or ethyl acetate is added. The resulting organic mixture is washed with an aqueous sodium chloride solution as required, and dried over a desiccant such as anhydrous magnesium sulfate, anhydrous sodium sulfate or anhydrous calcium chloride. The organic medium is then removed under reduced pressure to give a crude product. The crude product, if required, can be purified by purifying means such as column chromatography, thin-layer chromatography or liquid chromatography.

Thus, in accordance with the aforesaid process, the orthoester derivative of the 3,6,7-trisubstituted-bicyclo[3.3.0]-2-octene represented by the following formula (IV) is obtained.

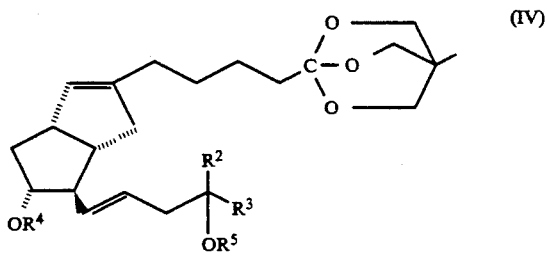

wherein $R^2$, $R^3$, $R^4$ and $R^5$ are the same as defined above.

The orthoester derivative of formula (IV) is subjected to a deprotection reaction, a hydrolysis reaction and an esterification reaction to afford the isocarbacylin derivative of formula (I) in this invention.

The removal of the protective group for the hydroxyl group may conveniently be carried out by using a catalyst such as acetic acid, pyridinium p-toluenesulfonate or a cation exchange resin in a reaction medium such as water, tetrahydrofuran, ethyl ether, dioxane, acetone or acetonitrile if the protective group is a group forming an acetal linkage together with the oxygen atom of the hydroxyl group. The reaction is usually carried out at a temperature of −78° C. to +30° C. for about 10 minutes to 3 days. If the protective group is a tri($C_1$–$C_7$)hydrocarbonsilyl group, the deprotection reaction is carried out at the same temperature in the aforesaid reaction solvent in the presence of e.g. acetic acid, tetrabutylammonium fluoride, cesium fluoride, aqueous hydrogen fluoride or pyridine-hydrogen fluoride.

The 4-methyl-2,6,7-trioxabicyclo[2.2.2]octo-1-yl group is converted into the 2,2-bis(hydroxymethyl)-propyloxycarbonyl group under the deprotection conditions of the protected hydroxyl group (e.g. under a catalyst such as acetic acid, a pyridinium p-toluenesulfonate or a cation exchange resin).

The 2,2-bis(hydroxymethyl)propyloxycarbonyl group is converted into a carboxyl group-containing compound under usual hydrolysis conditions of the ester group, i.e. by reaction with lithium hydroxide, sodium hydroxide or potassium hydroxide in water or a solvent containing water at −40° C. to 100° C., preferably 0° C. to 50° C. for 10 minutes to 24 hours.

In accordance with this invention, the carboxyl group-containing compound formed by the above hydrolysis reaction can be converted into the carboxylic acid ester derivative by the esterification reaction known per se if required.

The thus obtained compound of formula (I), the 3,6,7-trisubstituted bicyclo[3.3.0]-2-octene, acts to suppress cytotoxicity. When said compound is used for such purpose, a side effect such as an activity to suppress platelet aggregation or a blood pressure depressing is lessened, and it is expected to be used as an organo-therapeutic agent for organ damage.

The following Examples illustrate this invention more specifically. However, this invention is not limited thereto.

EXAMPLE 1

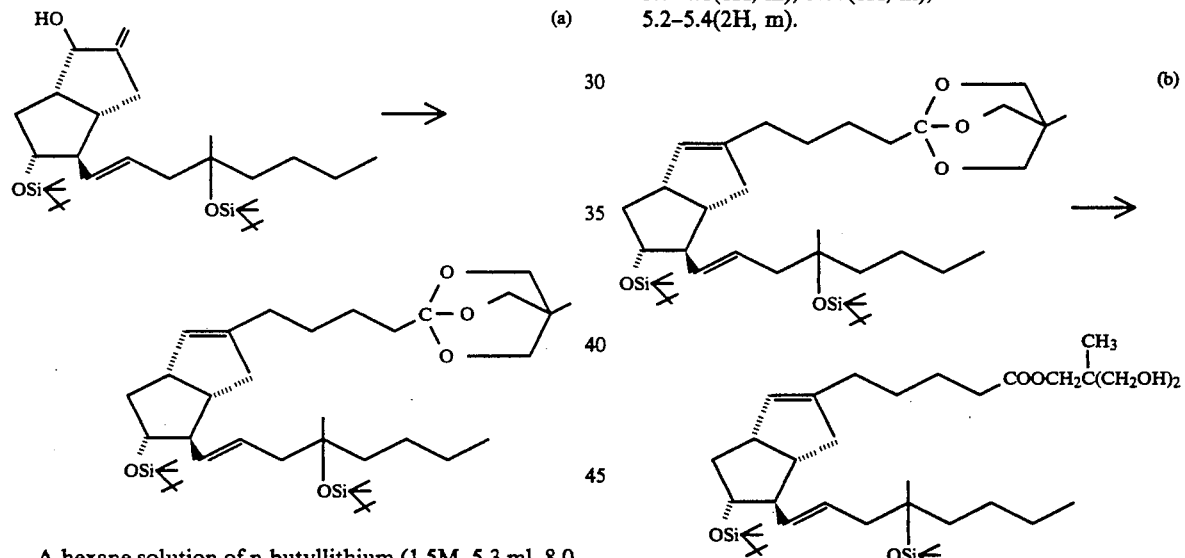

A hexane solution of n-butyllithium (1.5M, 5.3 ml, 8.0 mmoles) was added at 0° C. to a solution of (1S,2RS,5S,6S,7R)- 2-hydroxy-3-methylene-6-[(E)-4-t butyldimethylsilyloxy-4-methyl-1-octenyl]-7-t-butyldimethylsilyloxybicyclo[3.3.0]octane (3.47 g, 6.65 mmoles) in 20 ml of tetrahydrofuran, and the mixture was stirred at room temperature for 30 minutes. The solution was added to a suspension of cuprous iodide (1.90 g, 9.98 mmoles) cooled at −78° C. The temperature of the mixture was elevated to room temperature, and it was stirred for 30 minutes.

Separately, prior to the above procedure, metallic lithium (532 mg, 76.4 mmoles) was added to a solution of naphthalene (9.8 g, 76.4 mmoles) in 40 ml of tetrahydrofuran at room temperature. After the mixture was colored, it was cooled to 0° C. and stirred for 5 hours. A solution of 1,1,1-tris(hydroxymethyl)ethane orthoester (9.59 g, 38.2 mmoles) of 1-(3-bromopropyl)-4-methyl-2,6,7-trioxabicyclo[2.2.2]octane-4-bromobutanoic acid in 20 ml of tetrahydrofuran was added dropwise at −78° C. to the resulting solution, and the mixture was stirred at −78° C. for 5 minutes. The resulting solution was added dropwise at −78° C. to the solution prepared by the previous procedure, and the mixture was stirred for 10 minutes. A solution of N,N-methylphenylaminotributylphosphonium iodide (8.71 g, 20.0 mmoles) in 30 ml of N,N-dimethylformamide was added to the mixture. The cooling bath was removed, and the temperature was elevated. The mixture was then stirred at room temperature for 3 hours.

A saturated aqueous solution of ammonium chloride was added to the reaction solution, and the mixture was extracted with hexane. The resulting organic layer was washed with an aqueous sodium chloride solution, dried over anhydrous magnesium sulfate and concentrated to give a crude product. The crude product was subjected to column chromatography (silica gel treated with triethylamine; hexane/ether=9/1) to give (1S,5S,6S,7R)-3-[4-(4-methyl-2,6,7-trioxabicyclo[2.2.2]octo-1-yl)butyl]6-[(E)-4-t-butyldimeth ylsilyloxy-4-methyl-1-octenyl]-7-t-butyldimethylsilyloxybicyclo[3.3.0]-2-octene (2.88 g, 4.26 mmoles, 64 %).

NMR(CDCl$_3$) δ:
0.03(12H, s), 0.73(3H, s),
0.8–1.0(21H, m), 1.0–2.3(23H, m),
1.11(3H, s), 3.74(6H, s),
3.7–4.1(1H, m), 5.07(1H, m),
5.2–5.4(2H, m).

(1S,5S,6S,7R)-3-[4-(4-methyl-2,6,7-trioxabicyclo[2.2.2]octo-1-yl)butyl]-6-[(E)-4-t-butyldimethylsilyloxy-4-methyl-1-octenyl]-7-t-butyldimethylsilyloxybicyclo[3.3.0]-2-octene (2.88 g, 4.26 mmoles) obtained in (a) above was dissolved in 250 ml of methanol, and 100 mg of pyridinium p-toluenesulfonate was added, followed by stirring at room temperature for 18 hours. After methanol was distilled off under reduced pressure, ethyl acetate was added, and the mixture was washed with an aqueous sodium chloride solution. The resulting organic layer was dried over anhydrous magnesium sulfate and concentrated to give a crude product. The crude product was subjected to silica gel column chromatography (hexane:ethyl acetate=3:1) to afford 15-deoxy-16-hydroxy16-methyl-9(O)-methano-Δ$^{6(9\alpha)}$-prostaglandin I$_1$2,2bis(hydroxymethyl)propyl ester 11,16-bis(t-butyldimethylsilyl)ether (2.66 g, 3.83 mmoles, 90 %).

NMR(CDCl₃ )δ: 0.03(12H, s), 0.7–0.9(24H, m), 1.0–2.5(23H, m), 1.12(3H, s), 3.17(2H, bs), 3.40(4H, bs), 3.98(2H, s), 3.3–4.1(1H, m), 5.06(1H, m), 5.2–5.4(2H, m).

IR (liquid film): 3420, 3040, 1735, 1720, 1255, 1115, 1050, 970, 835, 770 cm⁻¹.

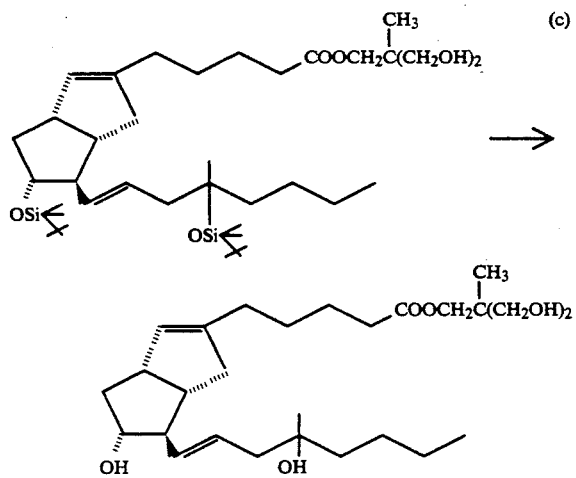

The 15-deoxy-16-hydroxy-16-methyl-9(0)-methano-Δ⁶⁽⁹ᵃ⁾- prostagrandin I1 2,2-bis(hydroxymethyl)propyl ester 11,16-bis(t-butyldimethylsilyl)ether (2.66 g, 3.83 mmoles) obtained in (b) above was dissolved in 150 ml of acetonitrile. Pyridine (3 ml) and then a hydrogen fluoride-pyridine complex (6 ml) were added, and the mixture was stirred at room temperature for 5 hours. The reaction solution was neutralized with sodium bicarbonate. The solution was extracted with ethyl acetate, then washed with an aqueous sodium chloride solution, dried over anhydrous magnesium sulfate and concentrated under reduced pressure to obtain a crude product. The crude product was subjected to silica gel column chlomatography (hexane:ethyl acetate=1:4) to afford 15-deoxy-16-hydroxy-16-methyl-9(O)-methano-Δ⁶⁽⁹ᵃ⁾-prostaglandin I₁ 2,2-bis(hydroxymethyl)propyl ester (1.44 g, 3.10 mmoles, 81%).

NMR(CDCl₃)δ: 0.84(6H, m), 1.0–3.1(27H, m), 1.11(3H, s), 3.40(4H, bs), 4.01(2H, s), 3.7–4.1(1H, m), 5.07(1H, m), 5.2–5.4(2H, m).

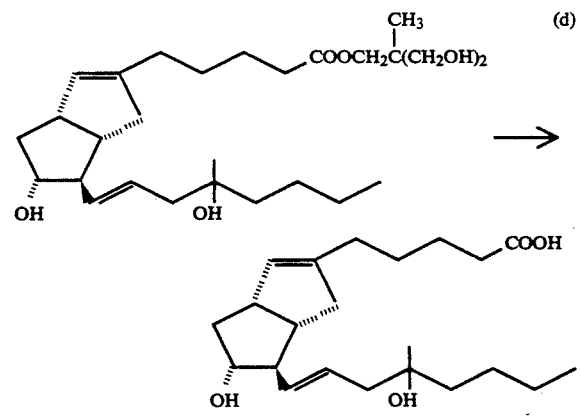

The 15-deoxy-16-hydroxy-16-methyl-9(0)-methano-Δ⁶⁽⁹ᵃ⁾- prostaglandin I1 2,2-bis(hydroxymethyl)propyl ester (1.44 g, 3.10 mmoles) obtained in (c) above was dissolved in a solvent mixture of 40 ml of tetrahydrofuran, 20 ml of methanol and 20 ml of water. Lithium hydroxide hydrate (1.30 g, 31 mmoles) was added thereto and stirred at room temperature for 18 hours. An aqueous ammonium chloride solution was added to the reaction liquid and the solvent mixture was then distilled off under reduced pressure. The resulting aqueous solution was acidified with dilute hydrochloric acid, extracted with ethyl acetate, washed with an aqueous sodium chloride solution, dried over anhydrous magnesium sulfate and then concentrated to obtain a crude product. The crude product was subjected to silica gel column chromatography (hexane:ethyl acetate=1:2) to afford 15-deoxy-16-hydroxy-16-methyl-9(O)-methano- Δ⁶⁽⁹ᵃ⁾-prostaglandin I₁(1.02 g, 2.79 mmoles, 90%).

NMR(CDCl₃)δ: 0.83(3H, m), 1.0–3.3(23H, m), 1.12(3H, s), 3.7–4.3(1H, m), 5.20(1H, bs), 5.3–5.5(2H, m), 6.27(3H, bs).

IR(liquid film): 3350, 3050, 1710, 1090, 970 cm⁻¹.

EXAMPLE 2

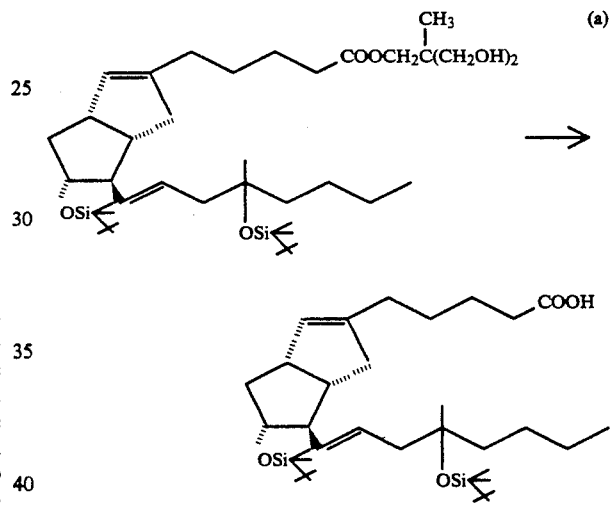

The 15-deoxy-16-hydroxy-16-methyl-9(0)-methano-Δ⁶⁽⁹ᵃ⁾-prostaglandin I1 2,2-bis(hydroxymethyl)propyl ester 11,16-bis(t-butyldimethylsilyl)ether (1.39 g, 2.00 mmoles) obtained in EXAMPLE 1(b) was dissolved in a solvent mixture of 60 ml of tetrahydrofuran, 30 ml of methanol and 20 ml of water, and 1.55 g of lithium hydroxide hydrate was added thereto, followed by stirring at room temperature for 20 hours. After an aqueous ammonium chloride solution was added, the solvent mixture was distilled off under reduced pressure, and the reaction mixture was acidified with dilute hydrochloric acid (pH of 3 to 4), and then extracted with ethyl acetate. The resulting organic layer was washed with an aqueous sodium chloride solution, dried over magnesium sulfate, and concentrated to obtain a crude product. The crude product was subjected to column chromatography (hexane:ethyl acetate=1:2) for purifieation to obtain 15-deoxy-16-hydroxy-16-methyl-9(O)-methano-Δ⁶⁽⁹ᵃ⁾-pros-taglandin I₁ 11,16-bis(t-butyldimethylsilyl)ether (1.14 g, 1.92 mmoles, 96%).

NMR(CDCl₃)δ: 0.03(12H, s), 0.8–1.0(21H), 1.13(3H, s), 1.0–1.6(12H, m), 1.7–3.1(11H, m), 3.3–4.1(1H, m), 5.23(1H, m), 5.4–5.5(2H, m), 9.73(1H, bs). IR(liquid film): 3040, 3000, 1710, 1255, 1115, 970, 850, 835, 775 cm⁻¹.

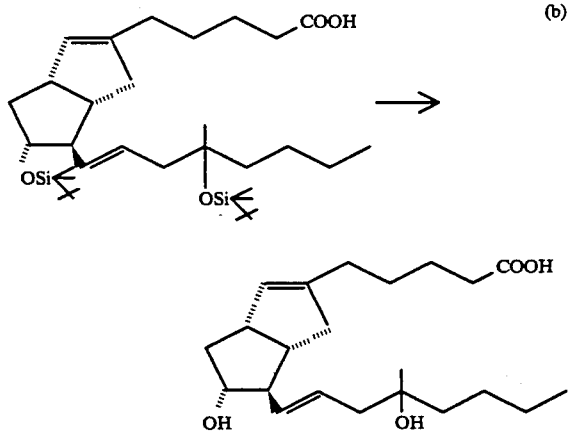

The 15-deoxy-16-hydroxy-16-methyl-9(O)-methano-Δ$^{6(9\alpha)}$-prostaglandin I$_1$ 11,16-bis(t-butyldimethylsilyl)ether (1.14 g, 1.92 mmoles) obtained in (a) above was deprotected with a hydrogen fluoride-pyridine complex under the same reaction conditions as in EXAMPLE 1(c), and treated and separated as in EXAMPLE 1(c) to afford 15-deoxy-16-hydroxy-16-methyl-9(O)-methano-Δ$^{6(9\alpha)}$-prostaglandin I$_1$ (0.59 g, 1.61 mmoles, 84 %). This product was completely identical with the product obtained in EXAMPLE 1(d).

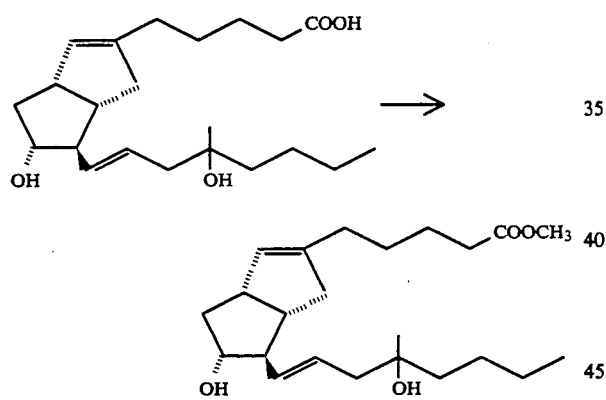

The 9(O)-methano-Δ$^{6(9\alpha)}$-prostaglandin I$_1$ (1.61 g, 4.42 mmoles) obtained in EXAMPLE 1(d) or 2(b) was dissolved in 150 ml of ether, and an ether solution of diazomethane was added at room temperature. After the reaction was over, the ether was distilled off under reduced pressure. There resulted 15-deoxy-16-hydroxy-16-methyl-9(O)-methano-Δ$^{6(9\alpha)}$prostaglandin I$_1$ methyl ester (1.71 g, 4.40 mmoles, 99%) as a nearly pure NMR(CDCl$_3$)δ: 0.83(3H, m), 1.1–3.1(25H, m), 1.13(3H, s), 3.65(3H, s), 3.9–4.3(1H, m), 5.23(1H, bs), 5.4–5.5(2H, m). IR(liquid film): 3350, 1740 cm$^{-1}$.

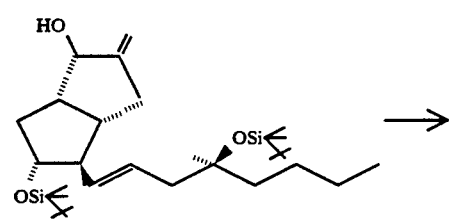

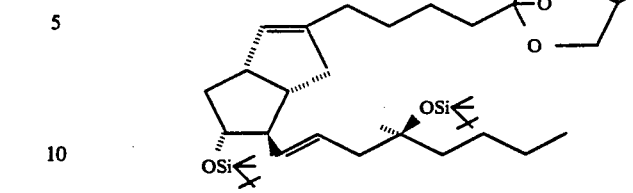

Using as a staring material (1S, 2RS,5S,6S,7R)-2-hydroxy-3-methylene-6-[(E,4S)4S-4-t-butyldimethyl-silyloxy-4-methyl-1-octenyl]- 7-t-butyldimethylsilyloxybicyclo[3.3.0]octane, (1S,5S,6S,7R)-3-[4-(4-methyl-2,6,7-trioxabicylclo[2.2.2]octo-1-yl)butyl-6-[(E,4S)-4-t-butyldimethylsilyloxy-4-methyl-1-octenyl]-7-t-butyl-dimethylsilyloxybicyclo[3 .3.0]-2-octene was obtained in the same way as in EXAMPLE 1. The yield was 72%. The spectral data completely agreed with that in EXAMPLE 1(a).

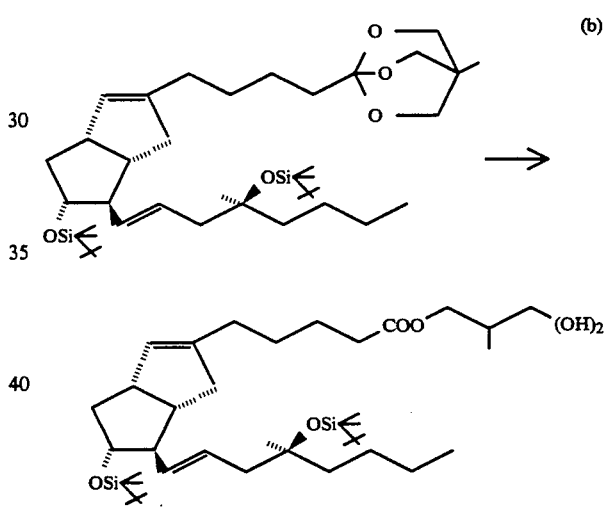

In the same way as in EXAMPLE 1(b), (16S)-15deoxy-16-hydroxy-16-methyl-9(O)-methano- Δ$^{6(9\alpha)}$-prostaglandin I$_1$ 2,2-bis(hydroxymethyl)propyl ester 11,16bis(t-butyldimethylsilyl)ether was obtained from (1S,5S,6S,7R)-3-[4-(4-methyl-2,6,7-trioxabicyclo[2.2.-2]octo-1-yl)butyl]-6-[(E, 4S)-4-t-butyldimethylsilyloxy-4methyl-1-octenyl]-7-t-butyldimethylsilyloxybicyclo[3.3.0]-2-octene formed in (a) above. The yield was 92%. Its spectral data completely agreed with that in EXAMPLE 1(b).

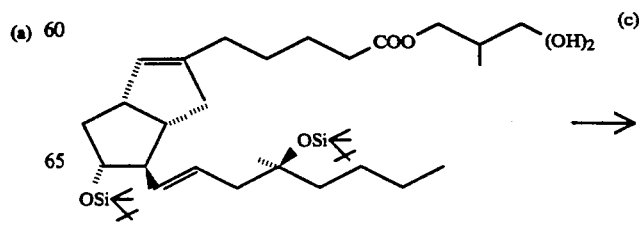

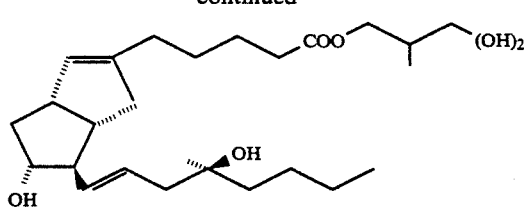

In the same way as in EXAMPLE 1(c), (16S)-15deoxy-16-hydroxy-16-methyl-9(0)-methano-Δ⁶⁽⁹ᵅ⁾-prostaglandin I₁ 2,2-bis(hydroxymethyl)propyl ester was obtained from (16S)-15-deoxy-16-hydroxy-16-methyl-9(O)-methano-Δ⁶⁽⁹ᵅ⁾-prostaglandin I₁ 2,2-bis(-hydroxymethyl)propyl ester 11,16-bis(t-butyldimethylsilyl)ether formed in (b) above. The yield was 86%. Its spectral data completely agreed with that in EXAMPLE 1(c).

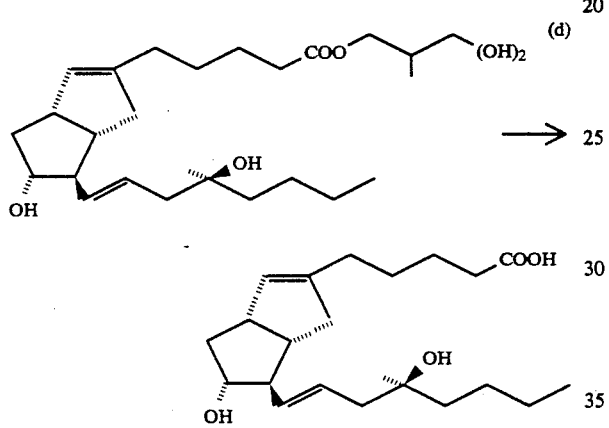

In the same way as in EXAMPLE 1(d), (16S)-15deoxy-16-hydroxy-16-methyl-9(O)-methano-Δ⁶⁽⁹ᵅ⁾-prostaglandin I₁ 16-methyl-9(0)-methano-Δ⁶⁽⁹ᵅ⁾-prostadeoxy-16-hydro 2,2-bis(hydroxymethyl)propyl ester formed in (c) above. The yield was 93%. Its spectral data agreed with that in EXAMPLE 1(d).

EXAMPLE 5

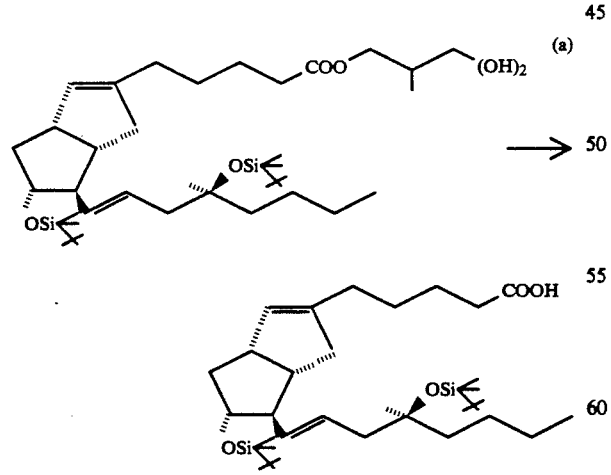

In the same way as in EXAMPLE 2(a), (16S)-15-deoxy-16-hydroxy-16-methyl-9(O)-methanoΔ⁶⁽⁹ᵅ⁾-prostagrandin I₁ 11,16-bis(t-butyldimethylsilyl)ether was obtained from (16S)-15-deoxy-16-hydroxy-16-methyl-9(O)-methano Δ⁶⁽⁹ᵅ⁾-prostagrandin I₁ 2,2-bis(hydroxymethyl)propyl ester 11,16-bis(t-butyldimethylsilyl)ether formed in EXAMPLE 4(b). The yield was 93%. Its spectral data agreed with that in EXAMPLE 2(a).

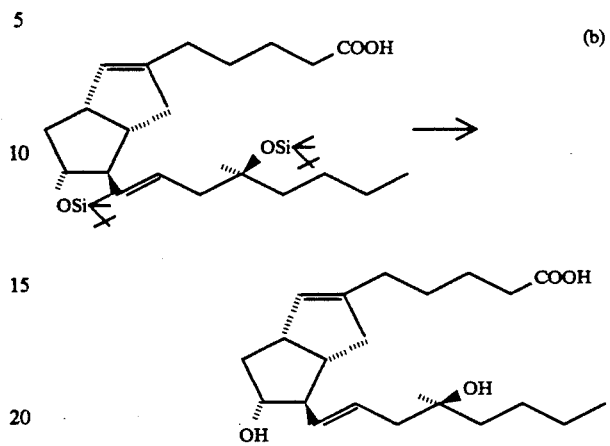

In the way as in EXAMPLE 2(b), (16S)-15deoxy-16-hydroxy-16-methyl-9(O)-methanoΔ⁶⁽⁹ᵅ⁾-prostaglandin I₁ was obtained rom (16S)-15deoxy-16-hydroxy-16methyl-9(O)-methanoΔ⁶⁽⁹ᵅ⁾-prostaglandin I₁ 11,16-bis(t-butyldimethylsilyl)ether formed in (a) above. The yield was 87%. This product was completely intentical with the product afforded in EXAMPLE 4(d).

EXAMPLE 6

In the same way as in EXAMPLE 7, (16S)-15deoxy-16-hydroxy-16-methyl-9(O)-methano-Δ⁶ ⁽⁹ᵅ⁾-prostaglandin I₁ methyl ester was obtained from (16S)-15-deoxy-16-hydroxy-16-methyl-9(O)-methanoΔ⁶⁽⁹ᵅ⁾-prostaglandin I₁ formed in EXAMPLE 4(d) or EXAMPLE 5(b). Its spectral data agreed with that in EXAMPLE 3.

EXAMPLE 7

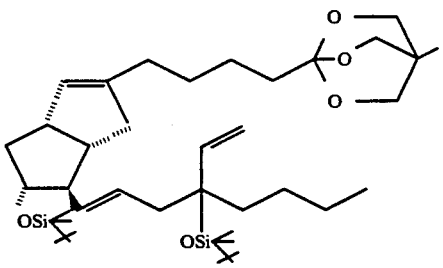

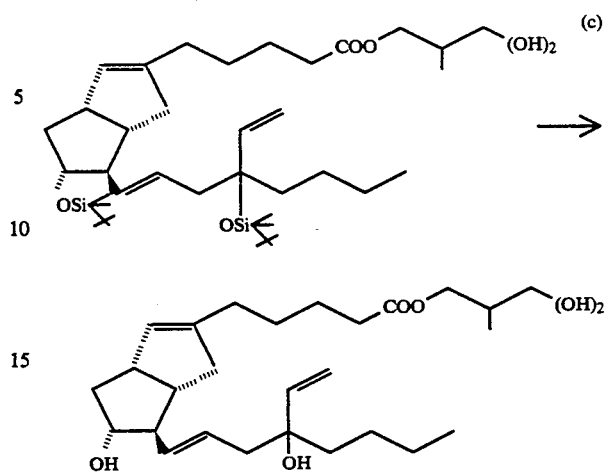

In the way way as in EXAMPLE 1(a), (1S,5S,6S,7R)-3-[4-(4-methyl-2,6,7-trioxybicyclo[2.2.2]octo-1-yl)butyl]-6-[(E)-4-t-butyldimethylsilyloxy-4-vinyl-1-octenyl]-7-t-butyldimethylsilyloxybicyclo[3.3.0]-2-octene was obtained from (1S,2RS,5S,6S,7R)-2-hydroxy-3-methylene-6-[(E)-4-t-butyldimethylsilyloxy4-vinyl-1-octenyl]-7-t-bu tyldimethylsilyloxybicyclo[3.3.0]octane. The yield was 67%.

NMR(CDCl$_3$)δ: 0.03(12H, s), 0.73(3H, s), 0.8-1.0(21H, m), 1.0-2.3(23H, m), 3.73(6H, s), 3.7-4.1(1H, m), 4.7-5.5(6H, m).

In the same way as in EXAMPLE 1(c), 15-deoxy16-hydroxy-16-vinyl-9(O)-methanoΔ$^{6(9α)}$-prostaglandin I$_1$ 2,2-bis(hydroxymethyl)propyl ester was obtained from 15-deoxy-16-hydroxy-16-vinyl-9(O)-methano-Δ$^{6(9α)}$-prostaglandin I$_1$ 2,2-bis(hydroxymethyl)propyl ester 11,16-bis(t-butyldimethylsilyl)ether formed in (c) above. The yield was 73%.

NMR(CDCl$_3$)δ: 0.84(6H, m), 1.0-3.1(27H, m), 3.40(4H, bs), 4.00(2H, s), 3.3-4.1(1H, m), 4.7-5.5(6H, m)

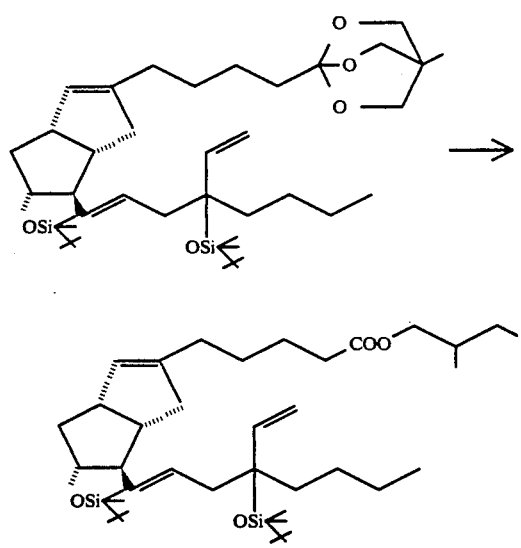

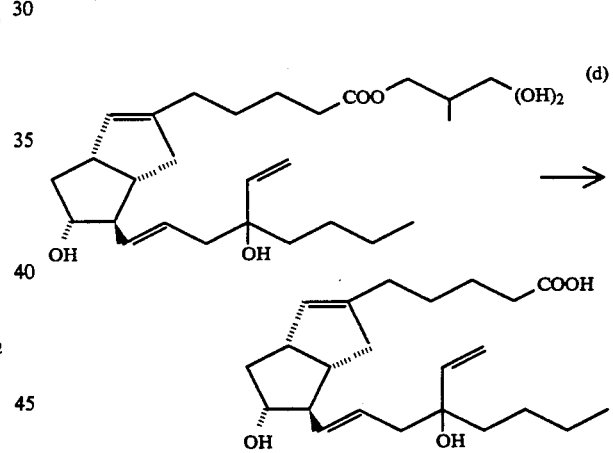

In the same way as in EXAMPLE 1(b), 15-deoxy16-hydroxy-16-vinyl-9(O)-methano-Δ$^{6(9α)}$-prostaglandin I$_1$ 2,2-bis(hydroxymethyl)propyl ester 11,16-bis(t-butyldimethylsilyl)ether was obtained from (1S,5S,6S,7R)--3-[4-(4-methyl-2,6,7-trioxabicyclo[2.2.2]octo-1-yl)butyl]-6-[(E)-4-t-butyldimethylsilyloxy-4-vinyl-1-octenyl]-7-t-butyldimethylsilyloxybicyclo[3.3.0]-2-octene formed in (a) above. The yield was 86%.

NMR(CDCl$_3$)δ: 0.03(12H, s), 0.7-0.9(24H, m), 1.0-2.5(23H, m), 3.08(2H, bs), 3.41(4H, bs), 3.98(2H, s), 3.3-4.1(1H, m), 4.7-5.5(6H, m).

IR(liquid film): 3420, 3080, 3040, 1735, 1720, 1645, 1255, 1115, 1050, 970, 835, 770 cm$^{-1}$.

In the same way as in EXAMPLE 4(d), the product formed in (c) above was converted into 15-deoxy-16-hydroxy-16-vinyl-Δ$^{6(9α)}$-prostaglandin I$_1$. The yield was 86%.

What we claim is:

1. An isocarbacyclin derivative represented by the following formula:

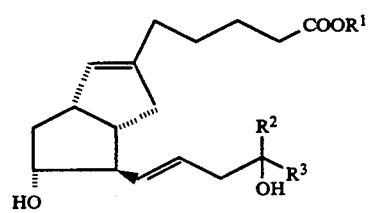

wherein R$^1$ represents H or methyl group, R$^2$ represents H, a methyl group or a vinyl group, and R$^3$ represents an unsubstituted linear or branched C$_3$-C$_8$ alkyl group or a $C_5$–$C_6$ cycloalkyl group, and a pharmaceuticaly acceptable salt thereof.

2. An isocarbacyclin derivative which is 15deoxy-16-hydroxy-16-methyl-9(O)-methano-$\Delta^{6(9\alpha)}$-prostaglandin $I_1$ of the formula:

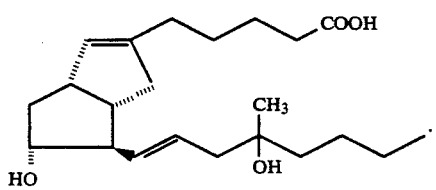

3. An isocarbacyclin derivative which is 15-deoxy-16-hydroxy-16-vinyl-9(O)-methano-$\Delta^{6(9\alpha)}$-prostaglandin $I_1$ of the formula:

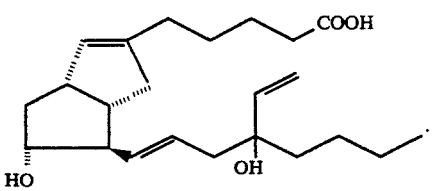

4. The isocarbacyclin derivative of claim 1 wherein $R^1$ represents H.

5. The isocarbacyclin derivative of claim 1 wherein $R^1$ represents methyl group.

* * * * *